United States Patent
Ye et al.

(10) Patent No.: US 7,828,481 B2
(45) Date of Patent: Nov. 9, 2010

(54) MEDICAL TABLE AND X-RAY IMAGING APPARATUS

(75) Inventors: Bin Ye, Beijing (CN); Jiake Xu, Beijing (CN); Shaobo Gu, Beijing (CN); Feng Wang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/238,093

(22) Filed: Sep. 25, 2008

(65) Prior Publication Data

US 2009/0086929 A1 Apr. 2, 2009

(30) Foreign Application Priority Data

Sep. 28, 2007 (CN) .................. 2007 1 0161308

(51) Int. Cl.
*A61B 6/04* (2006.01)
(52) U.S. Cl. ...................... 378/209; 378/117
(58) Field of Classification Search ............ 378/117, 378/116, 208, 209; 5/600–601; 600/427
See application file for complete search history.

(56) References Cited

U.S. PATENT DOCUMENTS

| 5,327,474 A | 7/1994 | Inoue et al. |
| 5,475,884 A | 12/1995 | Kirmse et al. |
| 5,661,772 A | 8/1997 | Bar et al. |
| 5,822,814 A | 10/1998 | Van der Ende |
| 5,825,843 A * | 10/1998 | Kobayashi .................. 378/20 |
| 5,832,056 A | 11/1998 | Mochitate et al. |
| 6,027,247 A | 2/2000 | Tachi et al. |
| 6,052,611 A | 4/2000 | Yanof et al. |
| 7,264,396 B2 | 9/2007 | Jahrling |

FOREIGN PATENT DOCUMENTS

JP 06-047040 2/1994

* cited by examiner

*Primary Examiner*—Hoon Song
(74) *Attorney, Agent, or Firm*—Armstrong Teasdale LLP

(57) ABSTRACT

A medical table wherein a top board on which a patient is placed is supported by a base having an internal instrument so as to be movable parallel to the board surface, the medical table includes a detecting device that detects the possibility that a hand or fingers, which grip the top board, come in contact with the internal instrument during the movement of the top board or internal instrument, and a preventing device that prevents the movement of the top board or the internal instrument on the basis of a detection signal of the detecting device.

20 Claims, 9 Drawing Sheets

MEDICAL TABLE AND X-RAY IMAGING APPARATUS

CROSS REFERENCE TO RELATED APPLICATIONS

This application claims the benefit of Chinese Patent Application No. 200710161308.4 filed Sep. 28, 2007, which is hereby incorporated by reference in its entirety.

BACKGROUND OF THE INVENTION

The subject matter disclosed herein relates to a medical table used for an X-ray imaging apparatus, and particularly to a medical table in which a top board, on which a patient is placed, is supported by a base having internal instruments so as to be movable parallel to the board surface.

A medical table used for an X-ray imaging is configured such that a top board on which a patient is placed is supported by a base. Internal instruments such as an X-ray receiver, X-ray film cassette, etc. are mounted in the base. These internal instruments receive X-ray that is emitted from an X-ray source through a patient and the top board. The top board is movable so as to be parallel to the board surface on the base (see, for example, Japanese Unexamined Patent Publication No. Hei 6 (1994)-47040).

The top board is manually moved by gripping the edge or the like of the top board with hand or fingers. The internal instruments are driven by a driving mechanism having power such as a motor so as to follow the movement of the X-ray source. In this case, precaution must be taken to prevent hand or fingers from being hit against the internal instruments or being caught in the internal instruments.

BRIEF DESCRIPTION OF THE INVENTION

It is desirable that the problem described previously is solved.

According to the first aspect of the invention, a medical table wherein a top board on which a patient is placed is supported by a base having an internal instrument so as to be movable parallel to the board surface, the medical table including: a detecting device that detects the possibility that a hand or fingers come in contact with the internal instrument during the movement of the top board or internal instrument; and a preventing device that prevents the movement of the top board or the internal instrument on the basis of the detection signal of the detecting device.

According to the second aspect, in the medical table described in the first aspect, the detecting device includes: a first detector that detects the collision of the hand or fingers with a limit line set at the top board to be parallel to the moving direction of the internal instrument; a second detector that detects the collision of the limit line with the moving area of the internal instrument in the moving direction of the top board vertical to the moving direction of the internal instrument; and a third detector that detects an offset of the top board in the direction in which the limit line collides with the moving area of the internal instrument, and wherein the preventing device has a first preventing device that prevents the movement of the top board on the basis of the detection signals of the first detector, second detector, and the third detector.

According to the third aspect, in the medical table described in the first aspect, the detecting device includes: a first detector that detects the collision of the hand or fingers with a limit line set at the top board so as to be parallel to the moving direction of the internal instrument; and a second detector that detects the collision of the limit line with the moving area of the internal instrument in the moving direction of the top board vertical to the moving direction of the internal instrument, and wherein the preventing device has a second preventing device that prevents the movement of the internal instrument on the basis of the detection signals of the first detector and the second detector.

According to the fourth aspect, in the medical table described in the second aspect or the third aspect, the first detector detects the collision of the hand or fingers with two limit lines set at both sides of the top board.

According to the fifth aspect, in the medical table described in the fourth aspect, the first detector is an optical detector.

According to the sixth aspect, in the medical table described in the fifth aspect, the optical detector includes an emitter and an optical sensor arranged at both ends of the limit line so as to be opposite to each other.

According to the seventh aspect, in the medical table described in the sixth aspect, the emitter is an infrared emitter.

According to the eighth aspect, in the medical table described in the second aspect or the third aspect, the second detector includes a first range specifying member that specifies the moving range of the top board in which the limit line does not collide with the moving area of the internal instrument; and a switch that relatively moves along the first range specifying member with the movement of the top board.

According to the ninth aspect, in the medical table described in the second aspect, the third detector includes a second range specifying member that specifies the range corresponding to a half of the length of the base in the direction vertical to the moving direction of the internal instrument; and a switch that relatively moves along the second range specifying member with the movement of the top board.

According to the tenth aspect, in the medical table described in the eighth aspect or the ninth aspect, the switch is a micro switch.

According to the other aspect, in the medical table described in the first aspect, the internal instrument is an X-ray receiver, or X-ray film cassette, or a housing having mounted thereto the X-ray receiver or X-ray film cassette.

According to the eleventh aspect, an X-ray imaging apparatus a medical table wherein a top board on which a patient is placed is supported by a base having an internal instrument so as to be movable parallel to the board surface; and an imaging device that images the patient placed onto the medical table with an X-ray, the X-ray imaging apparatus further including: a detecting device that detects the possibility that a hand or fingers, which grip the top board, come in contact with the internal instrument during the movement of the top board or internal instrument; and a preventing device that prevents the movement of the top board or the internal instrument on the basis of the detection signal of the detecting device.

According to the twelfth aspect, in the X-ray imaging apparatus described in the eleventh aspect, the detecting device includes: a first detector that detects the collision of the hand or fingers with a limit line set at the top board to be parallel to the moving direction of the internal instrument; a second detector that detects the collision of the limit line with the moving area of the internal instrument in the moving direction of the top board vertical to the moving direction of the internal instrument; and a third detector that detects an offset of the top board in the direction in which the limit line collides with the moving area of the internal instrument, and wherein the preventing device has a first preventing device that prevents the movement of the top board on the basis of the detection signals of the first detector, second detector, and the third detector.

According to the thirteenth aspect, in the X-ray imaging apparatus described in the eleventh aspect, the detecting device includes: a first detector that detects the collision of the hand or fingers with a limit line set at the top board to be parallel to the moving direction of the internal instrument; and a second detector that detects the collision of the limit line with the moving area of the internal instrument in the moving direction of the top board vertical to the moving direction of the internal instrument, and wherein the preventing device has a second preventing device that prevents the movement of the internal instrument on the basis of the detection signals of the first detector and the second detector.

According to the fourteenth aspect, in the X-ray imaging apparatus described in the twelfth aspect or in the thirteenth aspect, the first detector detects the collision of the hand or fingers with two limit lines set at both sides of the top board.

According to the fifteenth aspect, in the X-ray imaging apparatus described in the fourteenth aspect, the first detector is an optical detector.

According to the sixteenth aspect, in the X-ray imaging apparatus described in the fifteenth aspect, the optical detector includes an emitter and an optical sensor arranged at both ends of the limit line so as to be opposite to each other.

According to the seventeenth aspect, in the X-ray imaging apparatus described in the sixteenth aspect, the emitter is an infrared emitter.

According to the eighteenth aspect, in the X-ray imaging apparatus described in the twelfth aspect or in the thirteenth aspect, the second detector includes: a first range specifying member that specifies the moving range of the top board in which the limit line does not collide with the moving area of the internal instrument; and a switch that relatively moves along the first range specifying member with the movement of the top board.

According to the nineteenth aspect, in the X-ray imaging apparatus described in the twelfth aspect, the third detector includes: a second range specifying member that specifies the range corresponding to a half of the length of the base in the direction vertical to the moving direction of the internal instrument; and a switch that relatively moves along the second range specifying member with the movement of the top board.

According to the twentieth aspect, in the X-ray imaging apparatus described in the eighteenth aspect or in the nineteenth aspect, the switch is a micro switch.

According to another aspect, in an X-ray imaging apparatus described in the eleventh aspect, the internal instrument is an X-ray receiver or X-ray film cassette, or a housing having mounted thereto the X-ray receiver or X-ray film cassette.

According to the first aspect, the medical table wherein a top board on which a patient is placed is supported by a base having an internal instrument so as to be movable parallel to the board surface, includes a detecting device that detects the possibility that a hand or fingers, which grip the top board, comes in contact with the internal instrument during the movement of the top board or internal instrument, and a preventing device that prevents the movement of the top board or the internal instrument on the basis of the detection signal of the detecting device, whereby the medical table having high safety upon manually moving the top board can be realized.

According to the eleventh aspect, the X-ray imaging apparatus including: a medical table wherein a top board on which a patient is placed is supported by a base having an internal instrument so as to be movable parallel to the board surface; and an imaging device that images the patient placed onto the medical table with an X-ray, further includes: a detecting device that detects the possibility that a hand or fingers, which grip the top board, comes in contact with the internal instrument during the movement of the top board or internal instrument; and a preventing device that prevents the movement of the top board or the internal instrument on the basis of the detection signal of the detecting device, whereby the X-ray imaging apparatus having the medical table with high safety upon manually moving the top board can be realized.

According to the second and twelfth aspects, the detecting device includes: a first detector that detects the collision of the hand or fingers with a limit line set at the top board so as to be parallel to the moving direction of the internal instrument; a second detector that detects the collision of the limit line with the moving area of the internal instrument in the moving direction of the top board vertical to the moving direction of the internal instrument; and a third detector that detects an offset of the top board in the direction in which the limit line collides with the moving area of the internal instrument, and the preventing device has a first preventing device that prevents the movement of the top board on the basis of the detection signals of the first detector, second detector, and the third detector, whereby the collision of the hand or fingers with the internal instrument can be prevented.

According to the third and thirteenth aspects, the detecting device includes: a first detector that detects the collision of the hand or fingers with a limit line set at the top board so as to be parallel to the moving direction of the internal instrument; and a second detector that detects the collision of the limit line with the moving area of the internal instrument in the moving direction of the top board vertical to the moving direction of the internal instrument, and the preventing device has a second preventing device that prevents the movement of the internal instrument on the basis of the detection signals of the first detector and the second detector, whereby the collision of the hand or fingers with the internal instrument can be prevented.

According to the fourth and fourteenth aspects, the first detector detects the collision of the hand or fingers with two limit lines set at both sides of the top board, whereby the safety is secured at both sides of the top board.

According to the fifth and fifteenth aspects, the first detector is an optical detector, whereby the collision of the hand or fingers with the limit line can be detected in a non-contact manner.

According to the sixth and sixteenth aspects, the optical detector includes an emitter and an optical sensor arranged at both ends of the limit line so as to be opposite to each other, whereby the collision of the hand or fingers with the limit line can easily be detected.

According to the seventh and seventeenth aspects, the emitter is an infrared emitter, whereby the ray is not an eyesore.

According to the eighth and eighteenth aspects, the second detector includes: a first range specifying member that specifies the moving range of the top board in which the limit line does not collide with the moving area of the internal instrument; and a switch that relatively moves along the first range specifying member with the movement of the top board, whereby the configuration can be simplified.

According to the ninth and nineteenth aspects, the third detector includes: a second range specifying member that specifies the range corresponding to a half of the length of the base in the direction vertical to the moving direction of the internal instrument; and a switch that relatively moves along the second range specifying member with the movement of the top board, whereby the configuration can be simplified.

According to the tenth and twentieth aspects, the switch is a micro switch, thereby achieving space saving.

According to another aspect, the internal instrument is an X-ray receiver or X-ray film cassette, or a housing having mounted thereto the X-ray receiver or X-ray film cassette, whereby the X-ray imaging can appropriately be performed.

Further objects and advantages of the present invention will be apparent from the following description of the preferred embodiments of the invention as illustrated in the accompanying drawings.

DETAILED DESCRIPTION OF THE INVENTION

Figure 1:
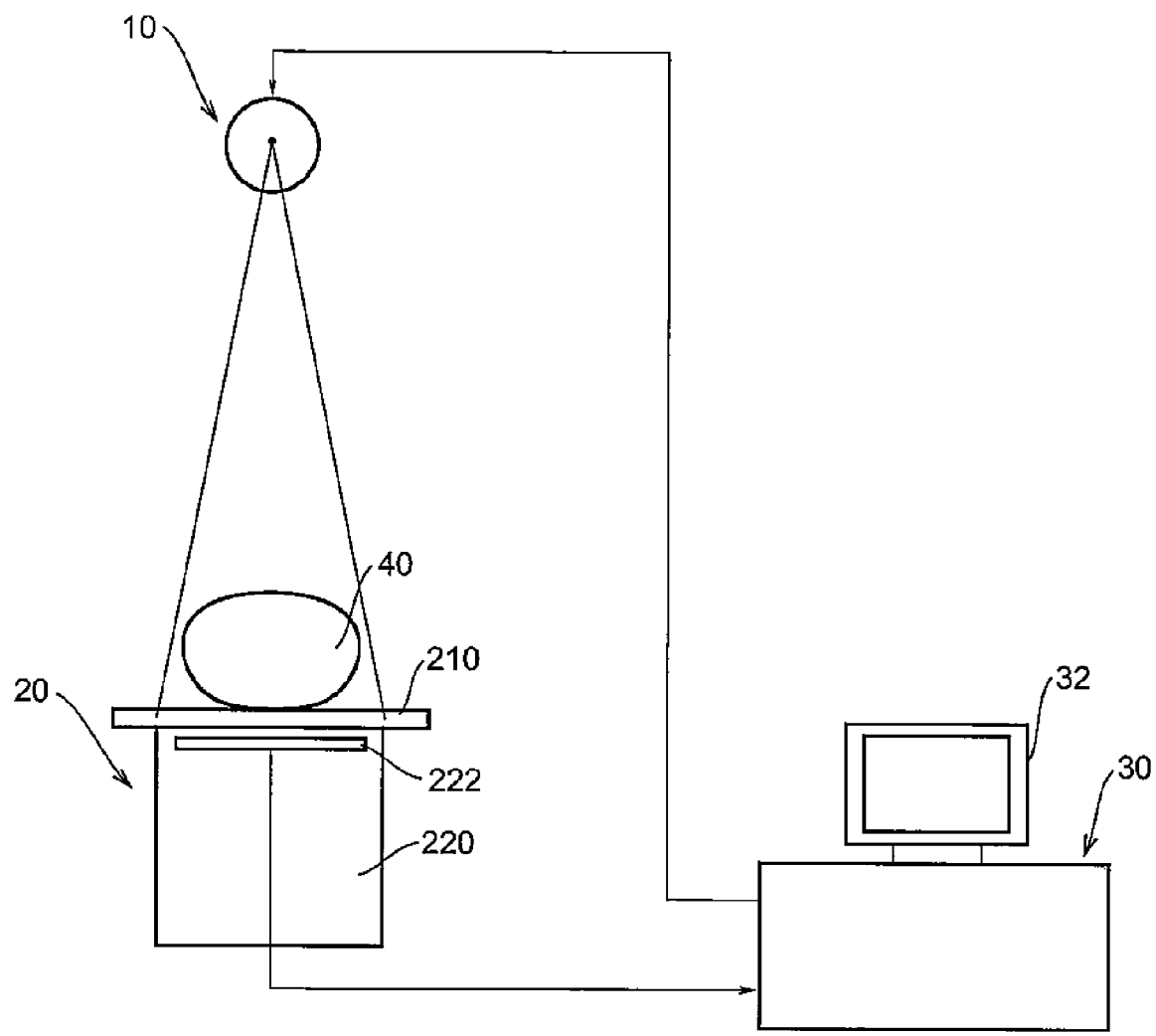
FIG. 1 is a view showing a configuration of an X-ray imaging apparatus.

Various embodiments of the invention will be explained below in detail with reference to the drawings. The invention is not limited to the embodiments described herein. FIG. 1 shows a schematic configuration of an X-ray imaging apparatus.

As shown in FIG. 1, the present apparatus has an X-ray irradiator 10, an imaging table 20, and an operator console 30. The imaging table 20 is configured such that a top board 210 is supported by a base 220. A patient 40 is placed on the top board 210. The base 220 has an X-ray receiver 222 incorporated therein. The X-ray irradiator 10 and the X-ray receiver 222 are opposite to each other so as to fluoroscope the patient 40 on the top board 210 with an X-ray.

The light-receiving signal of the X-ray receiver 222 is inputted to the operator console 30. The operator console 30 reconstructs the fluoroscopic image on the basis of the input signal, and displays the same onto a display 32. The fluoroscopic image can directly be imaged by using an X-ray film cassette, instead of the X-ray receiver 222. Explained below is the case in which the X-ray receiver 222 is used, but the same is true for the case of using the X-ray film cassette.

The operator console 30 controls the X-ray irradiator 10. The X-ray intensity of the X-ray irradiator 10 is controlled such that the brightness of the fluoroscopic image displayed on the display 32 becomes constant. The X-ray intensity is controlled by controlling the tube voltage or tube current of the X-ray tube in the X-ray irradiator 10. The operator console 30 also controls the position or height of the X-ray irradiator 10.

The X-ray irradiator 10, X-ray receiver 222 and operator console 30 are one example of imaging device in the invention. The imaging table 20 is one example of a medical table in the invention.

Figure 2:
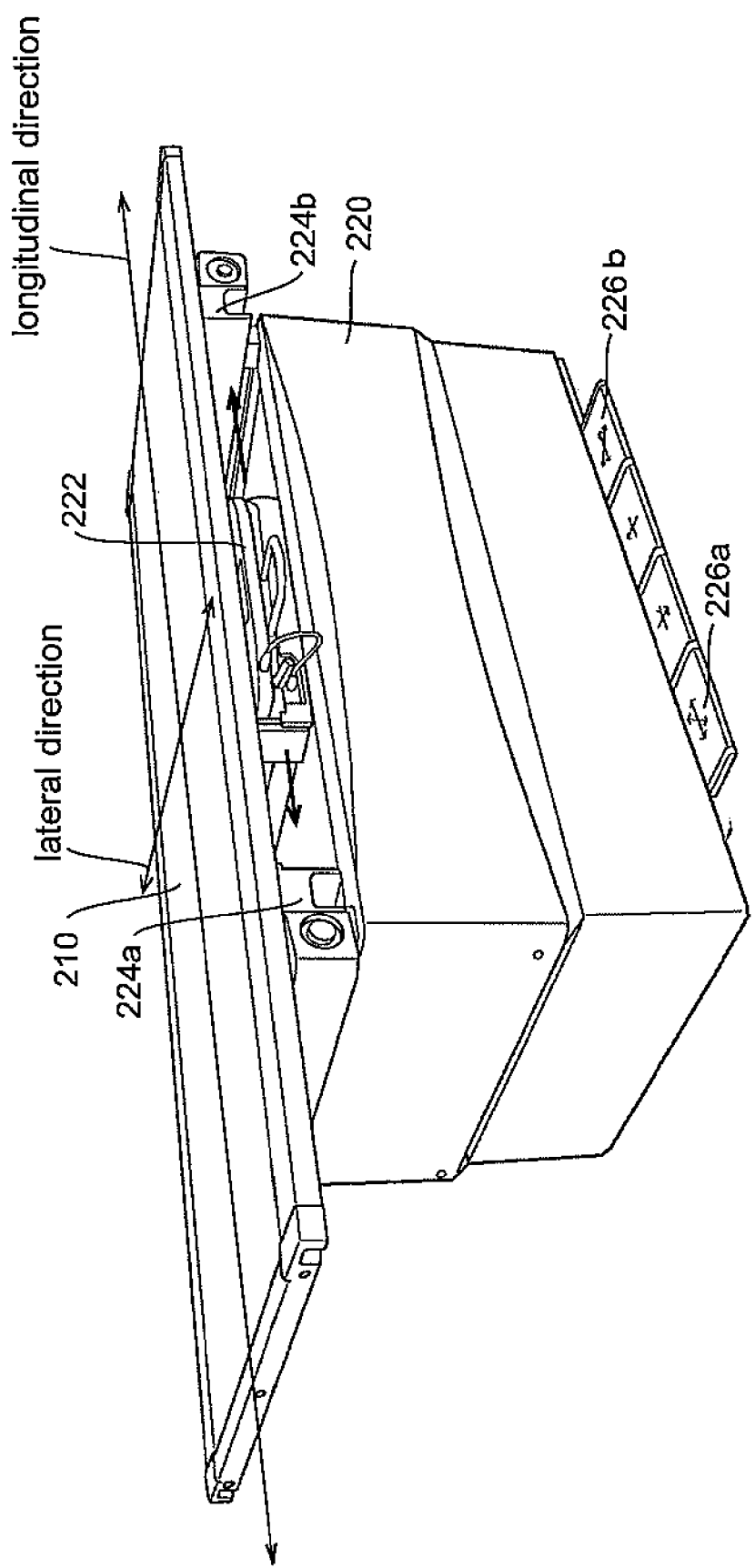
FIG. 2 is a view showing an appearance of a medical table may be used with the X-ray imaging apparatus shown in FIG. 1.

FIG. 2 shows an appearance of the imaging table 20. As shown in FIG. 2, the top board 210 has a rectangular flat-plate structure, and the base 220 has a generally rectangular solid box-like structure. The X-ray receiver 222 is arranged at the upper portion of the base 220 so as to oppose to the back surface of the top board 210. The direction parallel to the long side of the top board 210 is referred to as a longitudinal direction and the direction parallel to the short side thereof is referred to as a lateral direction below.

The base 220 has a pair of support beams 224a and 224b at its upper portion. The support beams 224a and 224b are beams extending in the lateral direction for movably supporting the top board 210. The movable direction of the top board 210 on the support beams 224a and 224b is the longitudinal direction indicated by an arrow.

The support beams 224a and 224b are supported so as to be movable in the lateral direction on the base 220. Thus, the top board 210 can be moved in the longitudinal direction and lateral direction with respect to the base 220. The support beams 224a and 224b move in the lateral direction together with the top board 210.

The top board 210 is always locked by a brake mechanism in the base 220, so that the top board 210 is immovable. The immovable state is hereinafter referred to as a locked state. The locked state is released by stepping on either one of right and left floating pedals 226a and 226b provided at the lower part of the base 220. Similar floating pedals are provided at the opposite side.

The locked state is released only during when the floating pedals 226a and 226b are stepped on, and during this period, the top board 210 is brought into movable state. The movable state is referred to as floating state below. The movement of the top board 210 by a manual operation is carried out in the floating state.

A control circuit in the base 220 controls the lock and floating of the bop board 210. The control circuit controls the lock and floating of the top board 210 on the basis of the input signal from the floating pedals 226a and 226b and the input signals from various sensors described later.

The X-ray receiver 222 is mounted to a housing that is movable in the longitudinal direction in the base 220. An X-ray film cassette can be mounted to the housing instead of the X-ray receiver 222. The X-ray receiver 222, X-ray film cassette and the housing having mounted thereto the X-ray receiver or X-ray film cassette are generically named a housing 222. The housing 222 is one example of the internal instruments in the invention.

The housing 222 is moved by a driving mechanism in the base 220 under the control of the operator console 30. The driving mechanism has a motor as a power source. The control circuit in the base 220 involves the control of the housing driving mechanism.

Figure 3:
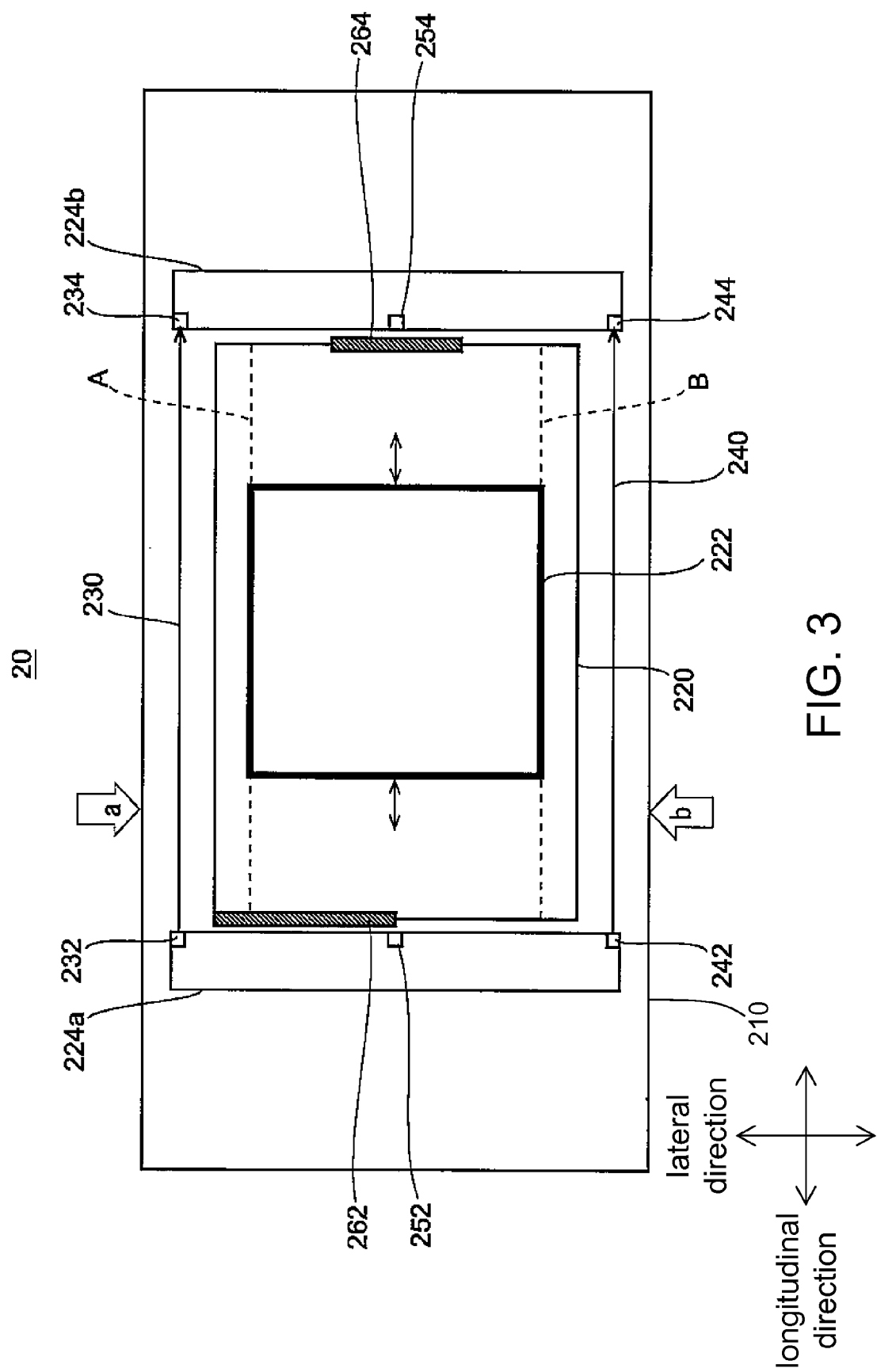
FIG. 3 is a view showing arrangements of various sensors in the medical table shown in FIG. 2.

FIG. 3 shows an arrangement of various sensors in the imaging table 20. FIG. 3 is a perspective view of the imaging table 20 vertically seen through the top board 210. The top board 210 is at the neutral position with respect to the base 220.

The locus of the movement of housing 222 in the longitudinal direction on the base 220 is indicated by two broken lines A and B. The area inside the broken lines A and B is a movable area of the housing 222. This area is the area where hand or fingers put therein might come in contact with or hit against the housing 222.

Emitters 232 and 242 are provided at both ends of the support beam 224a so as to direct toward the support beam 224b. On the other hand, optical sensors 234 and 244 are provided at both ends of the support beam 224b so as to direct toward the support beam 224a.

The emitter 232 and the optical sensor 234 are opposite to each other, so that the light from the emitter 232 is detected by the optical sensor 234. The emitter 242 and the optical sensor 244 are opposite to each other, so that the light from the emitter 242 is detected by the optical sensor 244.

Examples of the emitters 232 and 242 include an infrared emitter. Corresponding to this, an infrared sensor is used for the optical sensors 234 and 244. The emitters 232 and 242 may be emitters emitting visible light, and corresponding to this, the optical sensors 234 and 244 may be visible ray sensors.

When an optical path 230 linking the emitter 232 and the optical sensor 234 is blocked by hand or fingers, light does not enter the optical sensor 234. When an optical path 240 linking the emitter 242 and the optical sensor 244 is blocked by hand or fingers, light does not enter the optical sensor 244.

The optical sensors 234 and 244 become active and non-active according to whether the optical paths 230 and 240 are intercepted or not. Accordingly, whether hand or fingers go into the optical paths 230 and 240 or not can be detected by the active state or non-active state of the optical sensors 234 and 244. It is to be noted that the hand or fingers going into the optical paths 230 and 240 are not only the hand or fingers of an operator but also hand or fingers of the patient on the top board 210.

The optical paths 230 and 240 pass the portion inside the edge of the top board 210 by the distance corresponding to the length of fingers of an average operator. The emitters 232 and 243 and the optical sensors 234 and 244 are arranged so as to establish the optical paths described above.

The limit line for the entry of hand or fingers is set by the optical paths 230 and 240. The optical paths 230 and 240 are one example of a limit line in the invention. In the present specification, the entry of hand or fingers into the optical paths 230 and 240 is referred to as the collision of hand or fingers with the limit line. The emitter 232, optical sensor 234, emitter 242, and optical sensor 244 are one example of a first detector in the invention.

A switch 252 is provided at the central portion of the support beam 224a so as to direct toward the base 220. Corresponding to the switch, a counter member 262 is provided at the base 220. The counter member 262 is provided so as to face the switch 252 over a half-length of the base 220 in the lateral direction.

A switch 254 is provided at the central portion of the support beam 224b so as to direct toward the base 220. Corresponding to the switch, a counter member 264 is provided at the base 220. The counter member 264 is provided so as to face the switch 254 over a predetermined length of the base 220 in the lateral direction.

A micro switch is used as the switches 252 and 254, and a steel strip is used as the counter members 262 and 264, for example. The switches and counter members are not limited to the micro switch and steel strip, respectively. The combination of an optical switch and shielding member may be employed.

The switches 252 and 254 face the counter members 262 and 264 respectively at the neutral position of the top board 210. The switches 252 and 254 are in their non-active states when they face the counter members 262 and 264.

When the support beams 224a and 224b move in the lateral direction together with the top board 210 to be outside the ranges of the counter members 262 and 264, the switches 252 and 254 become active. The movements of the support beams 224a and 224b in the lateral direction represent the movement of the top board 210 in the lateral direction.

The movement of the top board 210 in the lateral direction includes the movement indicated by an arrow a in which the optical path 230 approaches one outer edge A of the movable area of the housing 222 and the movement indicated by an arrow b in which the optical path 240 approaches the other outer edge B of the movable area of the housing 222. The former movement is referred to as an offset A, while the latter movement is referred to as an offset B.

When the top board 210 moves in the direction of the offset A from the neutral position, the switch 252 deviates from the range of the counter member 262. Thus, the switch 252 becomes active. The active state of the switch 252 indicates that the top board 210 is in the state of the offset A.

When the top board 210 moves in the direction of the offset B from the neutral position, the switch 252 remains in the range of the counter member 262. Thus, the switch 252 remains non-active. The non-active state of the switch 252 indicates that the top board 210 is at the neutral position or in the state of the offset B.

Notably, the switch 252 may be active at the neutral position. This is possible by shortening the counter member 262 to a degree of not facing the switch 252 at the neutral position. The switch 252 and the counter member 262 are one example of a third detector in the invention. The counter member 262 is one example of a second range specifying member in the invention.

During when the switch 254 is within the range of the counter member 264 even if the top board 210 is in the state of the offset A or offset B, the switch 254 keeps its non-active state. When the offset distance exceeds the range set by the length of the counter member 264, the switch 254 becomes active. The range set by the length of the counter member 264 is referred to as a safety range.

Figure 4:
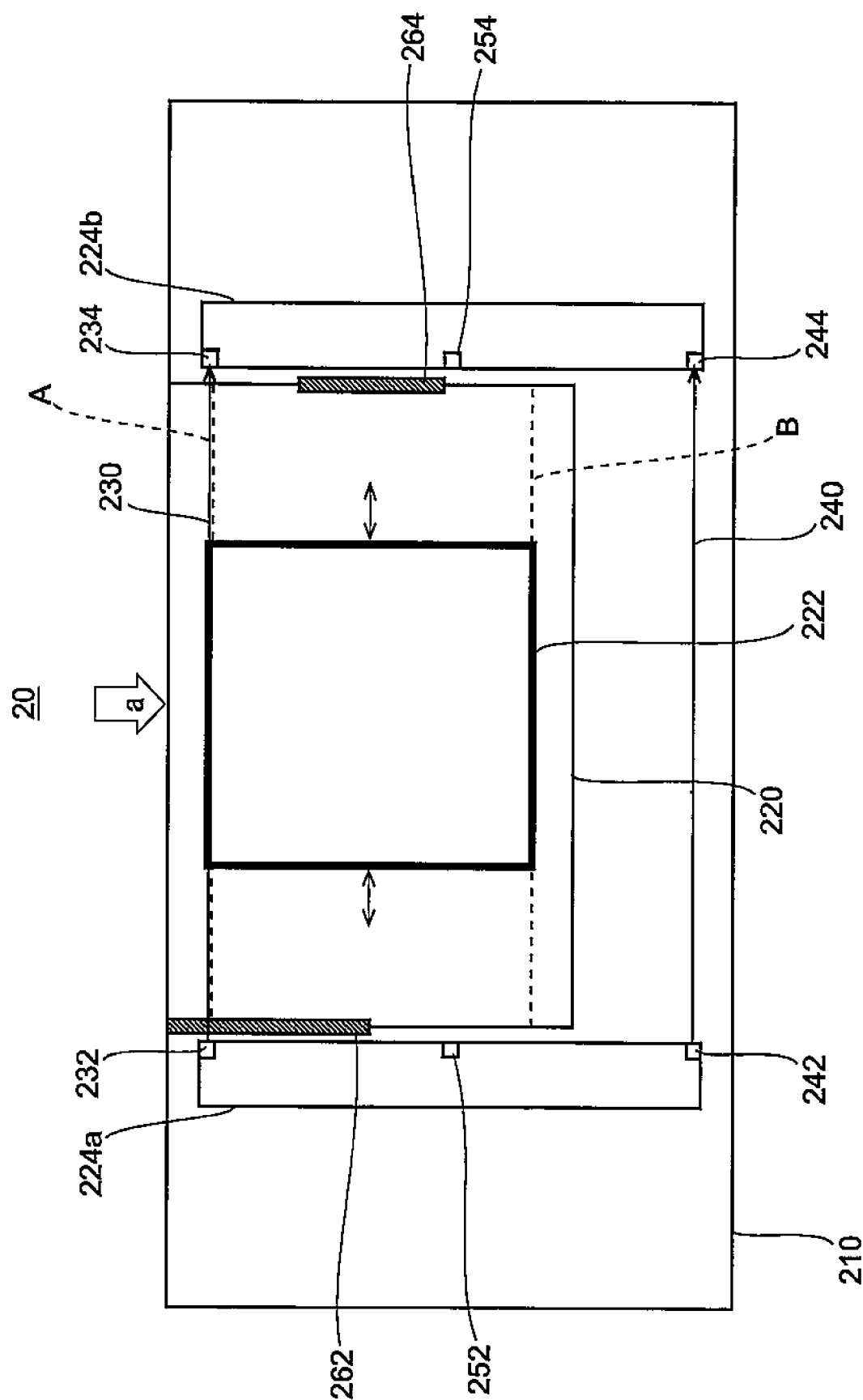
FIG. 4 is a view showing the state in which the offset of the top board exceeds the safety range.

FIG. 4 shows the state in which the offset A exceeds the safety range. As shown in FIG. 4, the top board 210 moves in the direction of an arrow a, so that the optical path 230 overlaps with one outer edge A of the movable area of the housing 222. It is to be noted that the optical path 230 is not blocked by the counter member 262. This state and the state in which the top board moves further in the direction a from this sate are referred to as a collision of the limit line with the movable area of the internal instruments in the present specification.

The safety range may be set to be about 5 mm short of the position where the optical path 230 overlaps with the outer edge A of the movable area of the housing 222. This can be realized by setting the length of the counter member 264 as the above-mentioned manner. In this case, the state in which the optical path 230 reaches the above-mentioned position and the state in which the optical path 230 further advances over the above-mentioned position are defined as the collision. The following explanation is made as the state in which the optical path 230 overlaps with the outer edge A of the movable area of the housing 222 and the state in which the optical path 230 further advances over the outer edge A are defined as the collision. The same is true for the case in which the optical path 230 reaches the position about 5 mm short of the position where the optical path 230 overlaps with the outer edge A and the optical path 230 further advances over the above-mentioned position.

In the collision state, the switches 252 and 254 are deviated from the ranges of the counter members 262 and 264 to become active. The active state of the switch 252 indicates that the top board 210 is in the state of the offset A, and the active state of the switch 254 indicates that the degree of the offset of the top board 210 corresponds to the collision.

Figure 5:
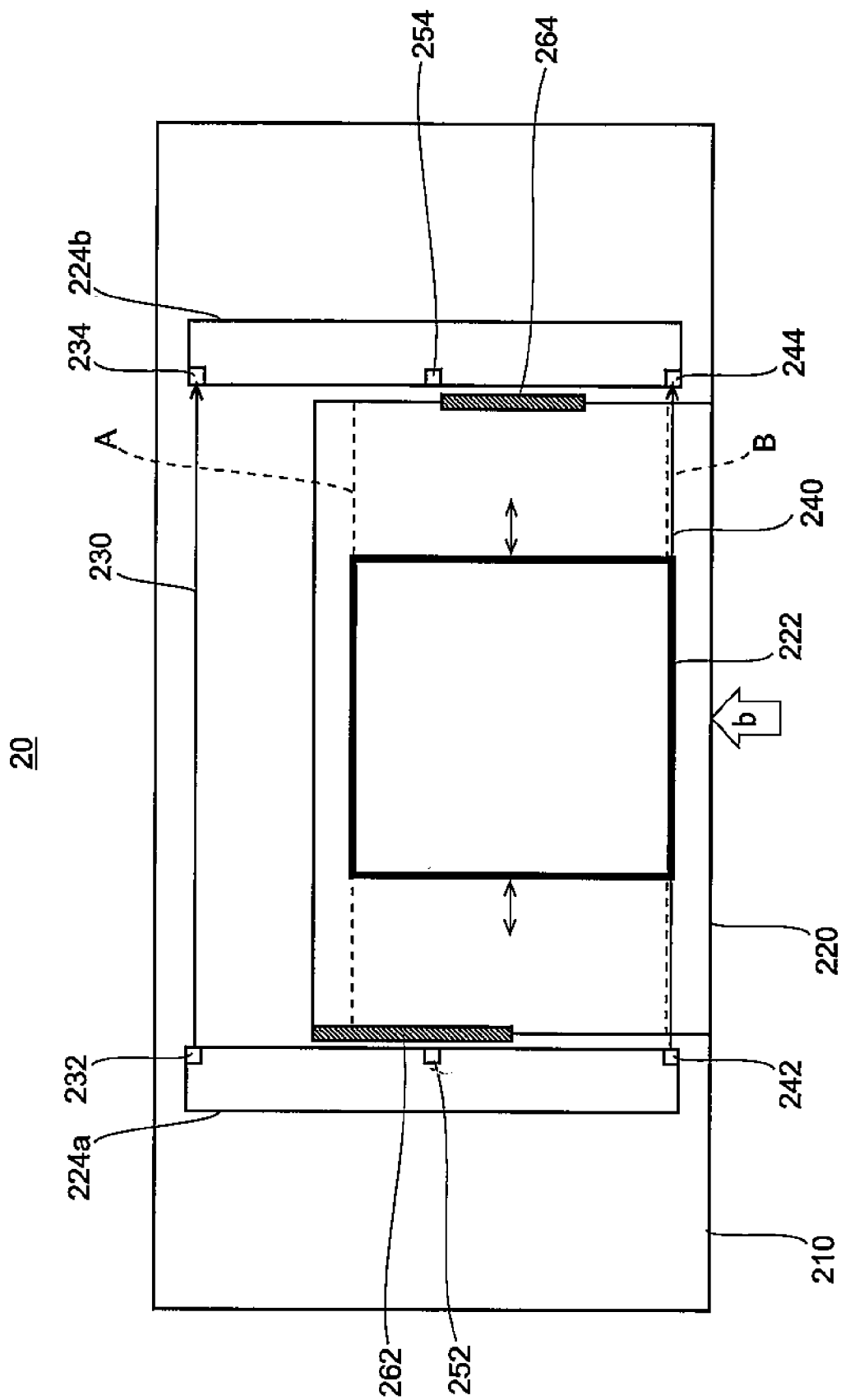
FIG. 5 is a view showing the state in which the offset of the top board exceeds the safety range.

FIG. 5 shows the state in which the offset B exceeds the safety range. As shown in FIG. 5, the top board 210 moves in the direction of an arrow b to reach the position where the optical path 240 overlaps with the other outer edge B of the movable area of the housing 222. With this state, the switch 252 is within the range of the counter member 262, while the switch 254 is outside the safety range.

Accordingly, the switch 252 is non-active, while the switch 254 is active. The non-active state of the switch 252 indicates that the top board 210 is in the state of the offset B, and the active state of the switch 254 indicates that the degree of the offset of the top board 210 corresponds to the collision. The switch 252 and the counter member 262 are one example of a second detector in the invention. The counter member 262 is one example of a first range specifying member in the invention.

Figure 6:
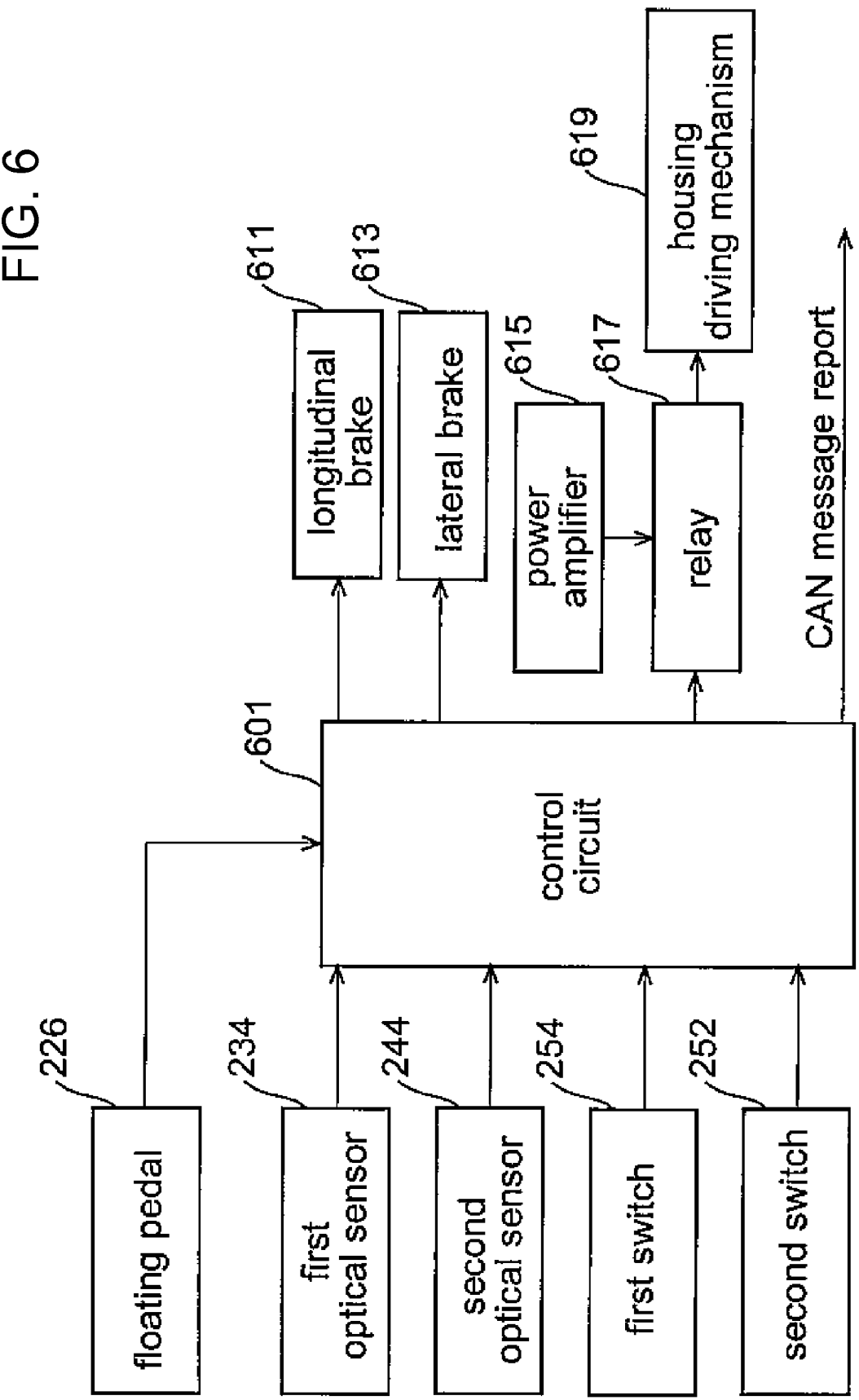
FIG. 6 is a block diagram of a table control system.

FIG. 6 is a block diagram of a table control system. As shown in FIG. 6, the table control system has a control circuit 601. The control circuit 601 is composed of, for example, a digital logic circuit or microcomputer.

The control circuit 601 controls a longitudinal brake 611, lateral brake 613, and relay 617 on the basis of the signals inputted from the floating pedal 226, first optical sensor 234, second optical sensor 244, first switch 254 and second switch 252. The control circuit 601 also transmits CAN message report (Controller Area Network message report) to the operator console 30.

The first optical sensor 234 and the second optical sensor 244 are the optical sensor 234 and the optical sensor 244 provided at both ends of the support beam 224b. The first switch 254 and the second switch 252 are the switch 254 and the switch 252 provided at the center of the support beams 224b and 224a. The optical sensors and switches are one example of detecting device in the invention.

The longitudinal brake 611 and the lateral brake 613 are those preventing the movement of the top board 210 in the longitudinal direction and lateral direction. The top board 210 is in its locked state or floating state by energizing or releasing the longitudinal brake 611 and the lateral brake 613. The longitudinal brake 611 and the lateral brake 613 are one example of a preventing device in the invention. The longitudinal brake 611 and the lateral brake 613 are also one example of a first preventing device in the invention.

The relay 617 intercepts the path for supplying an output signal to the housing driving mechanism 619 from a power amplifier 615. The path for supplying the output signal is intercepted by ON/OFF of the relay 617. The power amplifier 615 is controlled by the operator console 30 so as to output power for operating the housing driving mechanism 619. The relay 617 is one example of a preventing device in the invention. The relay 617 is also one example of a second preventing device in the invention.

Figure 7:
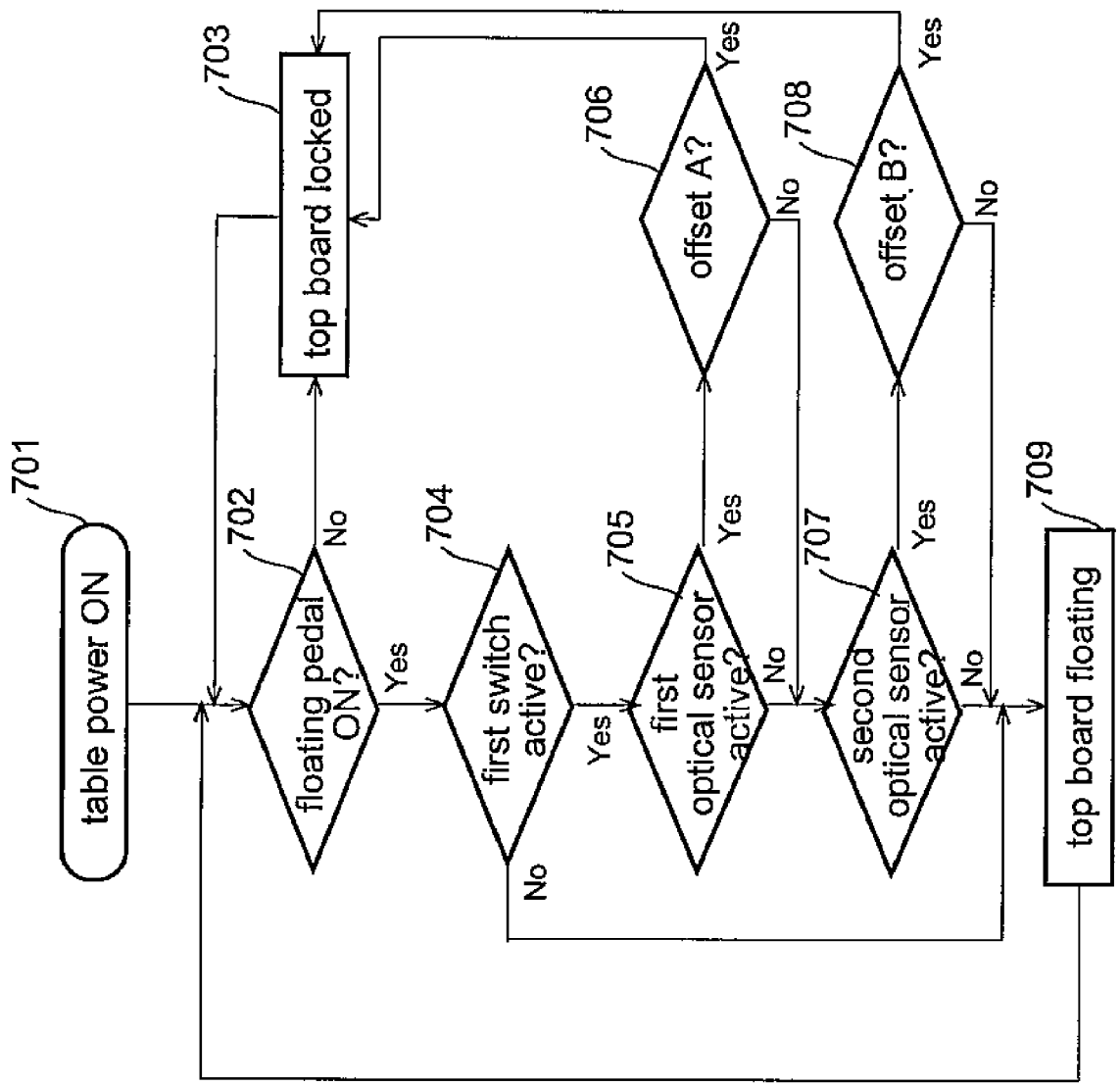
FIG. 7 is a flowchart of the operation of the table control system.

FIG. 7 shows a flowchart of one operation of the table control system. This flowchart shows the operation of the control circuit 601 for controlling the lock and floating of the top board 210. As shown in FIG. 7, the control of the top board is started by turning the table power ON at step 701.

It is determined at step 702 whether the floating pedal is ON or not. Whether the floating pedal is ON or not is determined on the basis of the input signal from the floating pedal 226. When the floating pedal is not ON, the top board is locked at step 703. The top board is locked by operating the longitudinal brake 611 and the lateral brake 613. By this operation, the top board 210 is in its locked state. When the floating pedal is not ON, the operations at steps 702 and 703 are repeated, so that the top board 210 is kept locked.

When the top board 210 is manually operated, an operator steps on the floating pedal 226. By this operation, the floating pedal is turned ON. The control circuit 601 determines this state at step 702, and proceeds to step 704.

It is determined at step 704 whether the first switch is active or not. Whether the first switch is active or not is determined on the basis of the input signal from the switch 254. The switch 254 becomes non-active or active depending upon whether the offset of the top board 210 is within or outside the safety range.

When it is determined that the first switch is non-active, the top board is floated at step 709. The top board 210 is floated by releasing the longitudinal brake 611 and lateral brake 613. By virtue of this operation, the top board 210 can be manually moved.

During when the floating pedal is ON and the first switch is non-active, the operations at steps 702, 704 and 709 are repeated. Accordingly, the floating state of the top board 210 is continued, whereby the operator can manually operate the top board 210.

When the offset of the top board 210 exceeds the safety range during the manual operation, the first switch becomes active. The control circuit 601 determines this state at step 704, and proceeds to step 705.

It is determined at step 705 whether the first optical sensor is active or not. Whether the first optical sensor is active or not is determined on the basis of the input signal from the optical sensor 234. The optical sensor 234 becomes active or non-active according to whether the optical path 230 is intercepted or not.

When the first optical sensor is active, it is determined at step 706 whether the offset of the top board 210 is the offset A or not. Whether the offset is the offset A or not is determined on the basis of the input signal from the switch 252. The input signal from the switch 252 indicates the offset A when it is active, and indicates the offset is not the offset A when it is non-active. When the offset is the offset A, the top board is locked at step 703. Thus, the top board 210 is in its locked state, so that the top board cannot be manually operated.

The fact that the first optical sensor is active and the offset is the offset A means that hand or fingers go into the optical path 230 and the optical path 230 collides with the movable range of the housing 222. Therefore, there is a fear of hand or fingers coming in contact with or hitting against the housing 222. In this case, the top board 210 is locked, whereby contact or collision of the hand or fingers to the housing 222 is forestalled.

When it is determined at step 706 that the offset is not the offset A, it is determined at step 707 whether the second optical sensor is active or not. Whether the second optical sensor is active or not is determined on the basis of the input signal from the optical sensor 244. The optical sensor 244 becomes active or non-active depending upon whether the optical path 240 is intercepted or not.

When the second optical sensor is active, it is determined at step 708 whether the offset of the top board 210 is the offset B or not. Whether the offset is the offset B or not is determined on the basis of the input signal from the switch 252. The input signal from the switch 252 indicates the offset B when it is non-active, and indicates the offset is not the offset B when it is active. When the offset is the offset B, the top board is locked at step 703. Thus, the top board 210 is in its locked state, so that the top board cannot be manually operated.

The fact that the second optical sensor is active and the offset is the offset B means that hand or fingers go into the optical path 240 and the optical path 240 collides with the movable range of the housing 222. Therefore, there is a fear of hand or fingers coming in contact with or hitting against the housing 222. In this case, the top board 210 is locked, whereby contact or collision of the hand or fingers to the housing 222 is forestalled.

When the first optical sensor is active, the offset is not the offset A, and the second optical sensor is non-active, the top board is floated at step 709. The similar operation is performed when the first optical sensor is non-active, the second optical sensor is active, and the offset is not the offset B. Therefore, the top board 210 is in its floating state, so that the manual operation can be continued.

The fact that the first optical sensor is active, the offset is not the offset A, and the second optical sensor is non-active means that hand or fingers go into the optical path 230 or the top board 210 is in the state of the offset B. Therefore, there is no fear of hand or fingers coming in contact with or hitting against the housing 222, whereby the floating state is maintained.

The fact that the first optical sensor is non-active, the second optical sensor is active, and the offset is not the offset B means that hand or fingers go into the optical path 240 or the top board 210 is in the state of the offset A. Therefore, there is no fear of hand or fingers coming in contact with or hitting against the housing 222, whereby the floating state is maintained.

Figure 8:
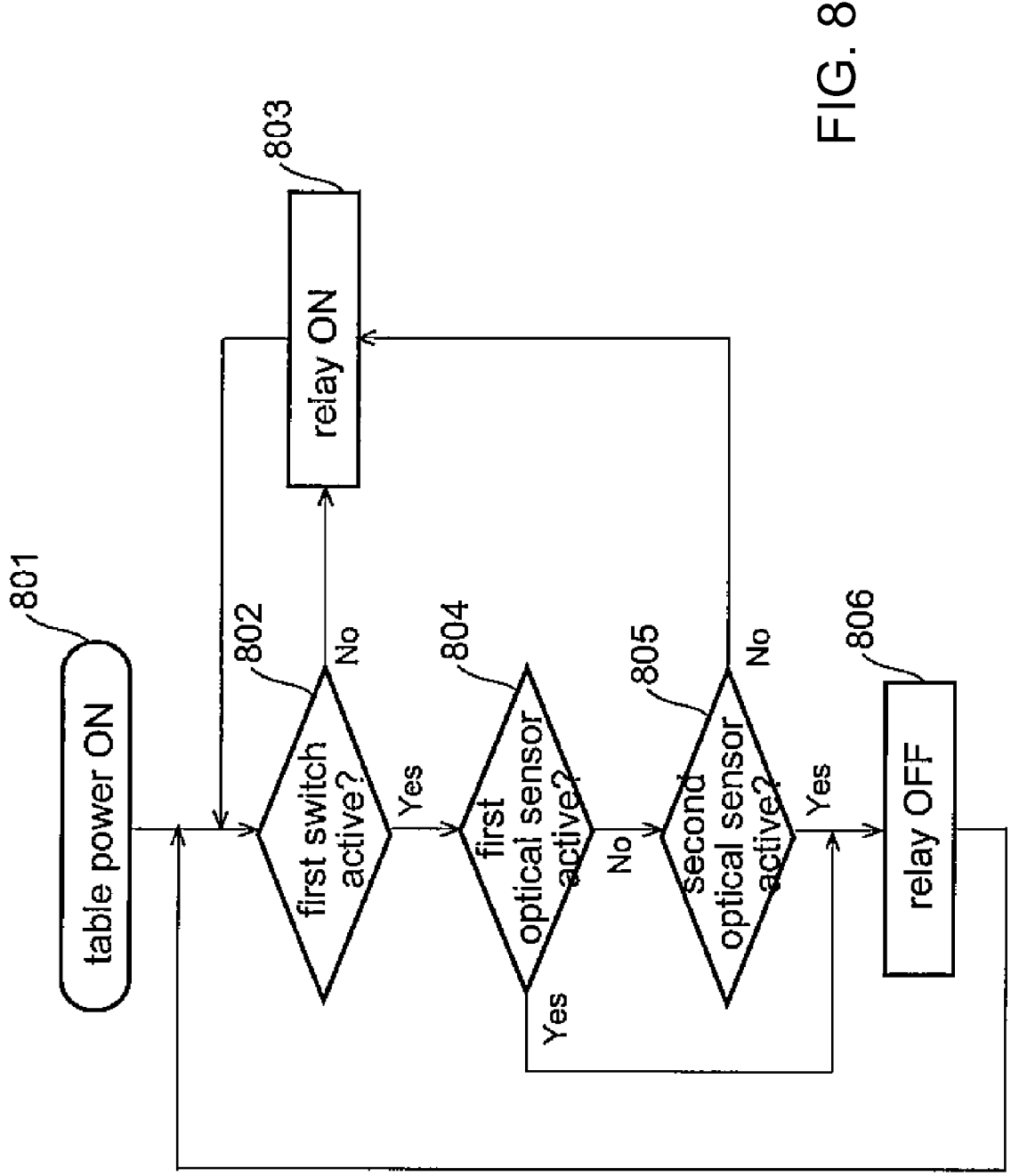
FIG. 8 is a flowchart of the operation of the table control system.

FIG. 8 shows a flowchart of the other operation of the table control system. This flowchart shows the operation of the control circuit 601 for controlling the relay 617. As shown in FIG. 8, the relay control is started when the table power is turned ON at step 801.

It is determined at step 802 whether the first switch is active or not. Whether the first switch is active or not is determined on the basis of the input signal from the switch 254. The switch 254 becomes non-active or active depending upon whether the offset of the top board 210 is within or outside the safety range.

When the first switch is non-active, the relay is turned ON at step 803. By this operation, the relay 617 is turned ON, so that the path for supplying power to the housing driving mechanism 619 from the power amplifier 615 is formed. Accordingly, the housing 222 is movable under the control of the operator console 30. During when the first switch is non-active, this state is maintained, and the movement of the housing 222 in the longitudinal direction is appropriately carried out by the operator console 30.

When it is determined at step 802 that the first switch is active, it is determined at step 804 whether the first optical sensor is active or not. Whether the first optical sensor is active or not is determined on the basis of the input signal from the optical sensor 234. The optical sensor 234 becomes active or non-active according to whether the optical path 230 is intercepted or not.

When it is determined that the first optical sensor is active, the relay-off is performed at step 806. By this operation, the relay 617 is turned OFF, so that the path for supplying power to the housing driving mechanism 619 from the power amplifier 615 is intercepted. Therefore, the movement of the housing 222 under the control of the operator console 30 becomes impossible.

The OFF of the relay 617 is transmitted to the operator console 30 as the CAN message report. The content of the CAN message report is displayed on the display 32 so as to report to the operator that the housing 222 is immovable.

The active state of the first optical sensor means that the hand or fingers go into the optical path 230. Since the movement of the housing 222 in the longitudinal direction becomes impossible by the OFF of the relay 617, the contact or collision of the hand or fingers to the housing 222 is forestalled.

When the first optical sensor is determined to be non-active at step 804, it is determined at step 805 whether the second optical sensor is active or not. Whether the second optical sensor is active or not is determined on the basis of the input signal from the optical sensor 244. The optical sensor 24 becomes active or non-active according to whether the optical path 240 is intercepted or not.

When the second optical sensor is determined to be active, the relay-off is performed. By this operation, the relay 617 is turned OFF, so that the path for supplying power to the housing driving mechanism 619 from the power amplifier 615 is intercepted. Therefore, the movement of the housing 222 under the control of the operator console 30 becomes impossible.

The OFF of the relay 617 is transmitted to the operator console 30 as the CAN message report. The content of the CAN message report is displayed onto the display 32 so as to report to the operator that the housing 222 is immovable.

The active state of the second optical sensor means that the hand or fingers go into the optical path 240. Since the movement of the housing 222 in the longitudinal direction becomes impossible by the OFF of the relay 617, the contact or collision of the hand or fingers to the housing 222 is forestalled.

When both the first optical sensor and the second optical sensor are non-active, the relay-on is continued at step 803. By this operation, the relay 617 is kept ON, so that the path for supplying power to the housing driving mechanism 619 from the power amplifier 615 is secured. Therefore, the movement of the housing 222 under the control of the operator console 30 becomes possible.

Figure 9:
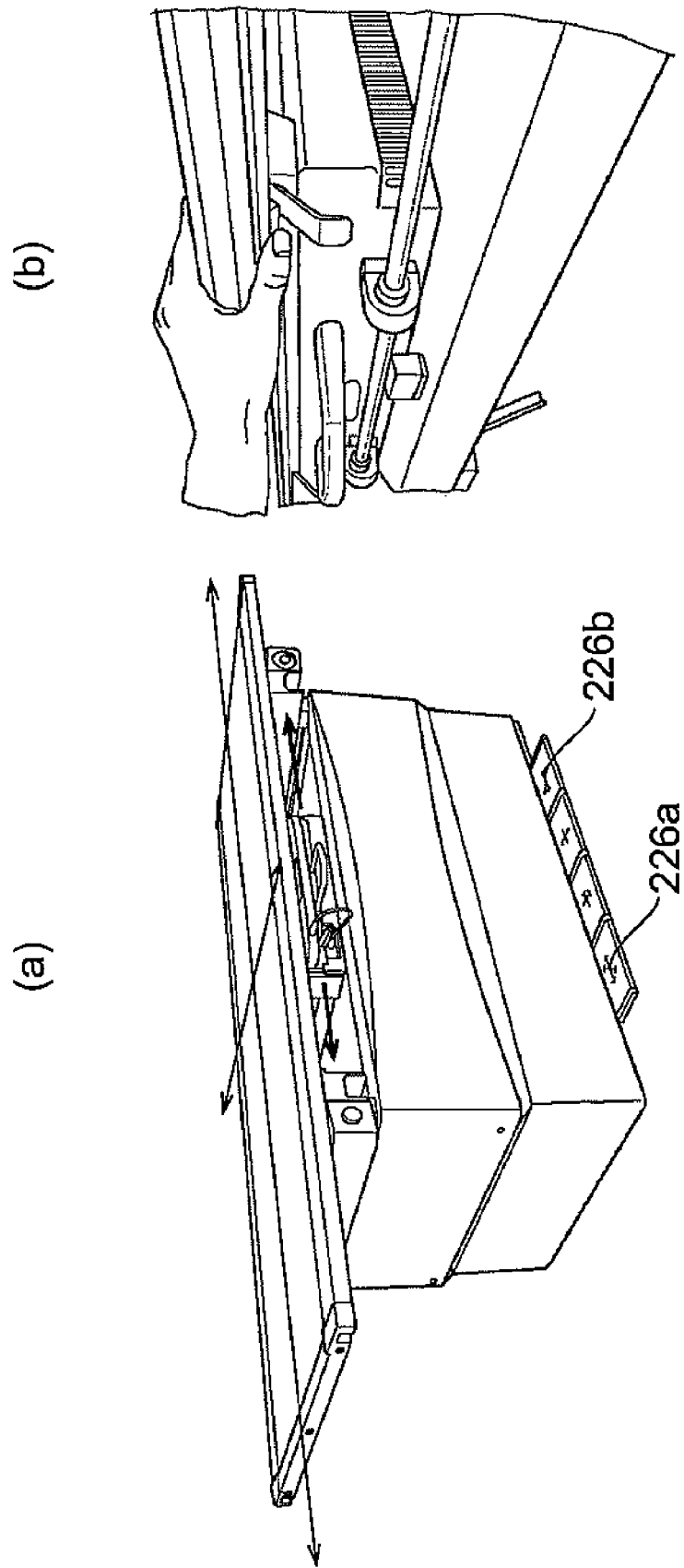
FIGS. 9(a) and 9(b) are views showing one example of a security.

The safety of the operator and patient can be secured by the control operation described above. FIGS. 9(a) and 9(b) show one example of security. If the floating pedal 226a or 226b is stepped on to bring the top board 210 in its floating state, and an operator grips the edge at the central portion of the top board 210 for moving the top board 210 in the lateral direction (push-in direction), when the top board 210 is at the neutral position as shown in FIG. 9(a), the hand or fingers of the operator arc about to come in contact with or hit against the housing 222. However, the top board 210 is automatically locked, thereby preventing an accident from happening.

If the operator grips the edge of the top board 210 as shown in 9(b) during the movement of the housing 222, there is a fear of the hand or fingers coming in contact with or hitting against the housing 222 or a fear of the hand or fingers nipped between the housing 222 and the top board 210. In this case, the movement of the housing 222 is inhibited, thereby preventing an accident from happening.

Many widely different embodiments of the invention may be configured without departing from the spirit and the scope of the present invention. It should be understood that the present invention is not limited to the specific embodiments described in the specification, except as defined in the appended claim.

What is claimed is:

1. A medical table comprising:
   a top board on which a patient is placed, said top board supported by a base comprising an internal instrument and configured to move parallel to a surface of said top board;
   a detecting device configured to detect a possibility that one of a hand and fingers, which grip the top board, will come into contact with said internal instrument during movement of one of said top board and said internal instrument, said detecting device comprising a first detector configured to detect a collision of one of the hand and the fingers with a limit line set at said top board to be parallel to a moving direction of said internal instrument; and a preventing device configured to prevent the movement of one of said top board and said internal instrument based on a detection signal generated by said detecting device.

2. A medical table according to claim 1, wherein said detecting device further comprises:

a second detector configured to detect a collision of the limit line with a moving area of said internal instrument in a moving direction of said top board vertical to the moving direction of said internal instrument; and a third detector configured to detect an offset of said top board in a direction in which the limit line collides with the moving area of said internal instrument, wherein said preventing device comprises a first preventing device configured to prevent the movement of said top board based on detection signals generated by said first detector, said second detector, and said third detector.

3. A medical table according to claim 1, wherein said detecting device further comprises a second detector configured to detect a collision of the limit line with a moving area of said internal instrument in a moving direction of said top board vertical to the moving direction of said internal instrument, wherein said preventing device comprises a second preventing device configured to prevent the movement of said internal instrument based on detection signals generated by said first detector and said second detector.

4. A medical table according to claim 1, wherein said first detector is further configured to detect the collision of one of the hand and the fingers with two limit lines set at both sides of said top board.

5. A medical table according to claim 4, wherein said first detector comprises an optical detector.

6. A medical table according to claim 5, wherein said optical detector comprises an emitter and an optical sensor arranged at both ends of the limit line so as to be opposite to each other.

7. A medical table according to claim 6, wherein said emitter comprises an infrared emitter.

8. A medical table according to claim 2, wherein said second detector comprises:

a first range specifying member configured to specify a moving range of said top board in which the limit line does not collide with the moving area of said internal instrument; and a switch configured to relatively move along said first range specifying member with the movement of said top board.

9. A medical table according to claim 2, wherein said third detector comprises:

a second range specifying member configured to specify a range corresponding to a half of a length of said base in a direction vertical to the moving direction of said internal instrument; and a switch configured to relatively move along said second range specifying member with the movement of said top board.

10. A medical table according to claim 8, wherein said switch comprises a micro switch.

11. An X-ray imaging apparatus comprising:

a medical table comprising a top board on which a patient is placed, said top board supported by a base comprising an internal instrument and configured to be movable parallel to a board surface;

an imaging device configured to image the patient;

a detecting device configured to detect a possibility that one of a hand and fingers, which grip the top board, will come into contact with said internal instrument during movement of one of said top board and said internal instrument, said detecting device comprising a first detector configured to detect a collision of one of the hand and the fingers with a limit line set at said top board to be parallel to a moving direction of said internal instrument; and a preventing device configured to prevent the movement of one of said top board and said internal instrument based on a detection signal generated by said detecting device.

12. An X-ray imaging apparatus according to claim 11, wherein said detecting device comprises:

a second detector configured to detect a collision of the limit line with a moving area of said internal instrument in a moving direction of said top board vertical to the moving direction of said internal instrument; and a third detector configured to detect an offset of said top board in a direction in which the limit line collides with the moving area of said internal instrument, wherein said preventing device comprises a first preventing device configured to prevent the movement of said top board based on detection signals generated by said first detector, said second detector, and said third detector.

13. An X-ray imaging apparatus according to claim 11, wherein said detecting device further comprises:

a second detector configured to detect a collision of the limit line with a moving area of said internal instrument in a moving direction of said top board vertical to the moving direction of said internal instrument, wherein said preventing device comprises a second preventing device configured to prevent the movement of said internal instrument based on detection signals generated by said first detector and said second detector.

14. An X-ray imaging apparatus according to claim 11, wherein said first detector is configured to detect the collision of one of the hand and the fingers with two limit lines set at both sides of said top board.

15. An X-ray imaging apparatus according to claim 14, wherein said first detector comprises an optical detector.

16. An X-ray imaging apparatus according to claim 15, wherein said optical detector comprises an emitter and an optical sensor arranged at both ends of the limit line so as to be opposite to each other.

17. An X-ray imaging apparatus according to claim 16, wherein said emitter comprises an infrared emitter.

18. An X-ray imaging apparatus according to claim 12, wherein said second detector comprises:

a first range specifying member configured to specify a moving range of said top board in which the limit line does not collide with the moving area of said internal instrument; and a switch configured to relatively move along said first range specifying member with the movement of said top board.

19. An X-ray imaging apparatus according to claim 12, wherein said third detector comprises:

a second range specifying member configured to specify a range corresponding to a half of a length of said base in a direction vertical to the moving direction of said internal instrument; and a switch configured to relatively move along said second range specifying member with the movement of said top board.

20. An X-ray imaging apparatus according to claim 18, wherein said switch comprises a micro switch.

* * * * *